United States Patent
Lindhofer et al.

(10) Patent No.: US 7,018,632 B2
(45) Date of Patent: Mar. 28, 2006

(54) METHOD FOR EX VIVO IMMUNIZATION USING HETEROLOGOUS INTACT BISPECIFIC AND/OR TRISPECIFIC ANTIBODIES

(75) Inventors: Horst Lindhofer, Gröbenzell (DE); Hans-Joachim Kolb, München (DE); Reinhard Zeidler, München (DE); Georg Bornkamm, München (DE)

(73) Assignee: GSF-Forschungszentrum für Umwelt und Gesundheit GmbH, Oberschleissheim (DE)

( * ) Notice: Subject to any disclaimer, the term of this patent is extended or adjusted under 35 U.S.C. 154(b) by 60 days.

(21) Appl. No.: 09/094,921

(22) Filed: Jun. 15, 1998

(65) Prior Publication Data

US 2002/0009430 A1    Jan. 24, 2002

(30) Foreign Application Priority Data

Jun. 17, 1997    (DE) ................................ 197 25 586

(51) Int. Cl.
*A61K 39/395* (2006.01)
*C12P 21/08* (2006.01)

(52) U.S. Cl. ................ 424/136.1; 424/130.1; 424/133.1; 424/277.1; 424/93.7; 424/9.71; 530/387.3

(58) Field of Classification Search ............. 424/277.1, 424/130.1, 133.1, 136.1, 138.1, 172.1, 173.1, 424/174.1, 93.71, 132.1, 135.1, 141.1, 143.1, 424/144.1, 152.1, 153.1, 154.1, 155.1, 156.1, 424/93.1, 93.21, 93.3, 93.7; 530/387.3

See application file for complete search history.

(56) References Cited

U.S. PATENT DOCUMENTS

| 4,844,893 | A | * | 7/1989 | Honsik et al. | |
| 5,484,596 | A | * | 1/1996 | Hanna et al. | ............ 424/277.1 |
| 5,837,243 | A | * | 11/1998 | Deo et al. | |
| 5,911,987 | A | * | 6/1999 | Volker et al. | |
| 5,985,276 | A |  | 11/1999 | Lindhofer et al. | |

FOREIGN PATENT DOCUMENTS

EP    0 826 695 A1    3/1998

OTHER PUBLICATIONS

Lindhofer, H. et al. Preferential species-restricted heavy/ligh chain pairing in rat/mouse quadromas. J. Immunology, 155: 219-225, 1995.*
Renner, C., et al, Science 264:833-835, 1994.*
H.G. Gottlinger et al. *Int. J. Cancer* (1986) 38: 47-53.
G.C. deGast et al. *Cancer Immunol Immunother* (1995) 40:390-396.
B.J. Kroesen et al. *Br. J. Cancer* (1994) 70: 652-661.
J-H. Qian et al. *The Journal of Immunology* (May 1, 1991) 146: 3250-3256.
R. Renner et al. *Cancer Immunol Immunother* (1997) 44: 70-76.
L.M. Weiner et al. *Cancer Research* (Oct. 15, 1995) 55: 4586-4592.
Lindhofer et al., "Bispecific antibodies target operationally tumor-specific antigens in two leukemia relapse models," *Blood* (1996) 88(12): 4651.
Lindhofer et al., "Increased tumor-specificity and -elimination by selectively binding bispecific antibodies in vivo," Abstract 348. ISSN: 0301-472X, XP002084410.
Lindhofer et al., "Bispecific antibodies effectively purge cancer cells from peripheral blood stem cell collections without affecting colony forming units," Abstract 527, ISSN: 0301-472X, XP002048523.
Wollenberg et al., "A bispecific antibody induces efficient killing of tumor cells: Phase I-trail in patients with HNSCC, " Abstract 15.16. ISSN: 00007-0920, XP002084411.

* cited by examiner

*Primary Examiner*—Alana M. Harris
*Assistant Examiner*—Anne L. Holleran
(74) *Attorney, Agent, or Firm*—Townsend and Townsend and Crew LLP

(57) ABSTRACT

According to the invention there is described a method for ex vivo immunization of humans and animals comprising the following steps:
  a) isolating autologous tumor cells;
  b) treating the tumor cells to prevent the survival thereof following reinfusion;
  c) incubating the thus treated tumor cells with intact heterologous bispecific and/or trispecific antibodies showing the following properties:
    α—binding to a T cell;
    β—binding to at least one antigen on a tumor cell;
    γ—binding, by their Fc portion (in the case of bispecific antibodies), or by a third specificity (in the case of trispecific antibodies) to Fc receptor-positive cells.

22 Claims, 6 Drawing Sheets

Figure 1A:
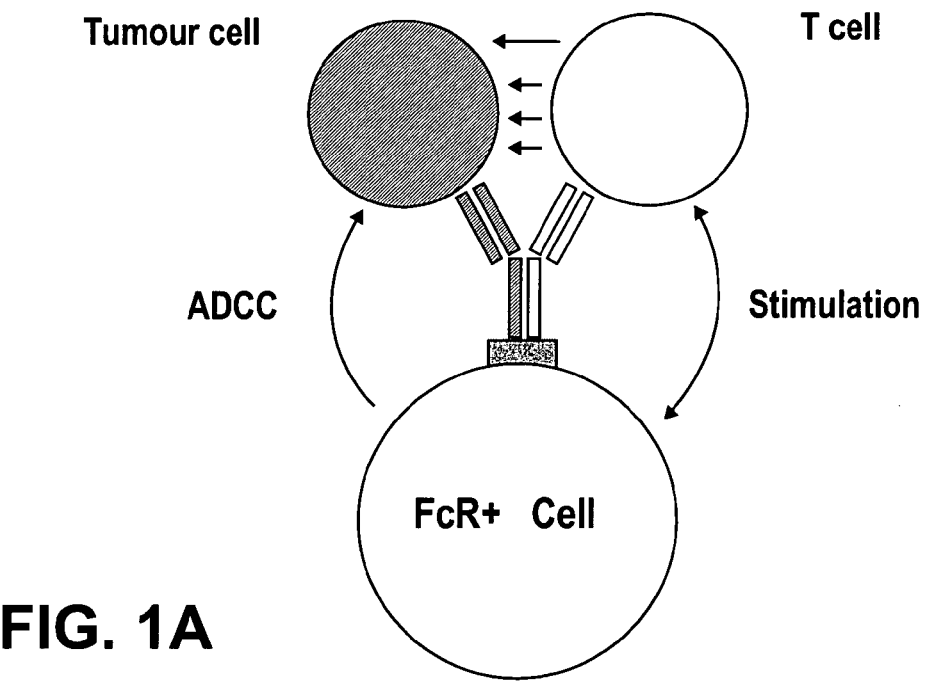

METHOD FOR EX VIVO IMMUNIZATION USING HETEROLOGOUS INTACT BISPECIFIC AND/OR TRISPECIFIC ANTIBODIES

The invention relates to a method for ex vivo immunization using heterologous, intact bispecific and/or trispecific antibodies as well as the use of the products of said method in the prevention and therapy of tumorous diseases and in particular in the induction of an anti-tumor immunity.

Despite the progresses in chemotherapy and radiotherapy achieved during recent years, malignant diseases in humans, for example advanced breast cancer, still have an extraordinarily unfavorable prognosis. Generally, such diseases are impossible to heal. Therefore, it is necessary to develop novel treatment strategies. In this respect, great hopes are placed on immunotherapeutic approaches which shall be used to induce the patient's immune system to reject the tumor. It is well known that tumor-associated antigens are present on tumor cells, and that in principle the immune system is very well able to recognize these antigens and to attack the malignant cells. However, tumors have developed various strategies which enable them to escape the immune reaction. They achieve this for example by an insufficient presentation of tumor-associated antigens and/or insufficient activation of tumor-specific T cells which are generally present.

With about 43,000 new cases/year, breast cancer occupies a top position in the cancer statistics of women in Germany. Less than one third of the women suffering from lymph node invasion at the time of diagnosis survive for 10 years without relapse.

To date, the immunotherapeutic approaches towards mamma carcinoma have been restricted to methods for unspecific stimulation, such as treatment by BCG or levamisole, and to the use of LAK and NK cells with IL-2 (3, 4). However, the types of immunotherapy employed provided no evidence for a prolongation of life; the treatment by BCG even proved to be disadvantageous (3). Since the unspecific activation of cells has not been very successful also in other types of tumor, attempts were made towards the induction of a specific immune reaction.

For example, T cell-redirecting bispecific antibodies were used in tumor therapy. These antibodies bind with one of their binding arms to a T cell receptor complex and with their other binding arm to a tumor-associated antigen on a tumor cell. The resulting activation of the T cell and the spatial proximity of the tumor cell leads to destruction of the latter by induction of apoptosis or by cytokines, such as TNF-$\alpha$ or perforin, respectively.

The antibodies used in tumor therapy in the prior art were directly infused into patients. This type of procedure shows several disadvantages:

it requires high doses of antibodies;
severe side effects may occur;
by their tumor binding arm the antibodies may also bind to normal tissue during in vivo application.

It is an object of the present invention to provide a novel method for the therapy of malignant diseases in humans, in particular with the objective of achieving an anti-tumor immunity.

According to the invention, this object has been achieved by the method characterized in more detail herein. Preferred embodiments of the method are also described herein.

The end product of the method of the present invention is a tumor cell preparation containing antibodies. This tumor cell preparation is used in the prevention and treatment of tumorous diseases by inducing an anti-tumor immunity.

By using the method of the present invention autologous tumor cells are treated with heterologous bispecific and/or trispecific antibodies, and the tumor cell preparation obtained by the present method is used for reinfusion into the patient or the animals from whom the autologous tumor cells have been obtained.

The invention relates further to the use of the method and the tumor cell preparations provided according to the invention in the prevention and therapy of tumorous diseases, in particular in the achievement of an anti-tumor immunity and particularly preferred of a long-term immunity.

The experiments provided in the present invention, particularly example 2, show that a long-lasting tumor immunity is provided. The results of the experiment performed in mice can be transferred also to humans. It is expected that a long-term immunity of several years can be provided by using the present invention. A tumor cell as described in the present invention is every cell which has lost its normal function by one or more mutations or wherein its normal function has been changed. Due to these mutations the tumor cells are able to propagate in an uncontrolled manner.

Tumor immunity according to the present invention is defined by activating the immune system of the body in an organism against the autologous tumor in such a way that a long-term or even permanent destruction and/or control of the autologous tumor is achieved.

According to the invention every kind of tumor falling under the definition given above can be treated by the present method. Particularly epithelial tumors, adenocarcinomas, colon carcinomas, mamma carcinomas, ovarial carcinomas, carcinomas of lungs, throat, nose and ear can be treated. Furthermore, preferably non-epithelial tumors like leukaemias and lymphomas and virus induced tumors like liver tumors or cervix carcinomas can be treated.

According to the invention, heterologous intact bispecific and/or trispecific antibodies are used. These antibodies are contacted ex vivo with tumor cells (autologous tumor cells) previously obtained from a patient. To prevent the survival of tumor cells following reinfusion, the tumor cells were treated in a manner known per se, such as by irradiation, prior to contacting with the antibodies. Following irradiation, the tumor cells are incubated with the intact heterologous bispecific and/or trispecific antibodies. According to the invention, not any antibody may be used but only antibodies which are intact, i.e. having a functional Fc portion, and they must be heterologous in nature, i.e. such antibodies which consist of heavy immunoglobulin chains of different subclasses (subclass combinations, also fragments) and/or origin (species).

These intact heterologous bispecific and/or trispecific antibodies will be selected to further have the following properties:

$\alpha$—binding to a T cell;
$\beta$—binding to at least one antigen on a tumor cell;
$\gamma$—binding, by their Fc portion (in the case of bispecific antibodies), or by a third specificity (in the case of trispecific antibodies) to Fc receptor-positive cells.

In a particularly preferred embodiment of the present invention the intact heterologous bispecific and/or trispecific antibodies are selected to be able to activate the Fc receptor-positive cell, and thereby inducing or increasing the expression of cytokines and/or co-stimulatory antigens. The tumor cell preparation obtained including said antibodies is then prepared further for reinfusion. It is transferred for instance in a device suitable for reinfusion.

In the case of trispecific antibodies, binding to the Fc receptor-positive cells preferably takes place via the Fc receptor of Fc receptor-positive cells or also via other antigens on Fc receptor-positive cells (antigen-presenting cells), such as the mannose receptor.

Only the present method and the use of the antibodies described herein ensure the development of an anti-tumor immunity after reinfusion of the antibodies into the patient from whom the tumor cells have previously been obtained. Preferably, reinfusion is carried out in a patient after treatment of the primary tumor, preferably in patients in a minimal residual disease (MRD) situation. In patients with few residual tumor cells but with a high risk of relapse, use of the method provided according to the invention will be particularly successful.

By using the method of the invention, it is possible to avoid the disadvantages known from the prior art and described in more detail above.

The heterologous bispecific and/or trispecific antibodies useful according to the invention are in part known per se, but in part they are described for the first time in the present application. An example for a bsab is antibody anti-CD3x anti-epcam which is employed in epithelial tumors such as mamma carcinoma.

According to the invention, two variations of the method may be distinguished:
1. short-term incubation, and
2. long-term incubation.

A short-term incubation is an incubation of the autologous tumor cells with intact heterologous bispecific and/or trispecific antibodies for a period of 10 minutes to 5 hours, or 10 minutes to 3 hours, or further preferred for a period of about 15 minutes to 2 hours, further preferred for a period of 15 minutes to 1 hour. The tumor cells charged with antibodies in this way are then prepared for reinfusion.

The long-term incubation is an incubation of the autologous tumor cells also for a period of about 10 minutes to 5 hours, preferably for a period of 15 minutes to 2 hours and further preferred for a period of 15 minutes to 1 hour, so that the autologous tumor cells are charged with antibodies. Subsequently, blood cells of the patient, preferably mononucleated cells of the peripheral blood (PBMCs=peripheral blood mononucleated cells) are added, and this mixture is then incubated over a prolonged period, such as 1 to 14 days, preferably 3 to 10 days and further preferred 6 to 10 days. Alternatively, another way of proceeding is contacting the autologous tumor cells directly with the bispecific and/or trispecific antibodies and with the patient's blood cells, preferably peripheral blood mononucleated cells. In this way, "priming" of numerous immune cells against the tumor is achieved already ex vivo. Afterwards, these cells are reinfused into the patient. Long-term incubation also leads to internalization and degradation of the antibodies.

Preliminary in vitro results show that immune cells pretreated in the way described are able to destroy tumor cells without further addition of bispecific and/or trispecific antibodies (cf. Example 1).

In short-term as well as long-term incubation, the T cells are redirected to the tumor cells by the bispecific and/or trispecific antibodies which are immobilized on the tumor cells; at the same time binding of Fc receptor-positive cells to the Fc portion of the bispecific and/or trispecific antibody takes place after reinfusion. This leads to activation of Fc receptor-positive cells by their binding to the Fc portions of immobilized (on the T cell or tumor cell, respectively) intact bispecific antibodies.

To enhance the success of immunization, the tumor cells treated with the antibodies either according to the short-term incubation method or the long-term incubation method may be administered to the patient not only once but optionally also several times.

On the tumor cell, an up-regulation of MHC 1 as well as activation of the intracellular processing machinery (proteasome complex) occurs due to the release of cytokines (such as INF-γ and TNF-α) in direct proximity of the tumor cell. Cytokines are released because of the bispecific antibody-mediated activation of T cells and accessory cells (see FIGS. 1 and 3). I.e. by the intact bsab not only tumor cells are destroyed and phagocytized but indirectly also their anti-tumor immunity is increased.

Activation of the Fc receptor-positive cells by the bsab depends on the subclass or subclass combination, respectively, of the bsab. As demonstrated in in vitro experiments, for example bsabs of the subclass combination mouse IgG2a/rat IgG2b are able simultaneously to bind to and activate Fc receptor-positive cells leading to up-regulation and formation (expression), respectively, of co-stimulatory antigens, such as CD40, CD80, or CD86, on the cell surface of such cells. In contrast, bsabs of the subclass combination mouse IgG1/IgG2b are able to bind to Fc receptor-positive cells (1) but clearly are unable to activate these cells to a comparable extent (2).

Figure 1B:
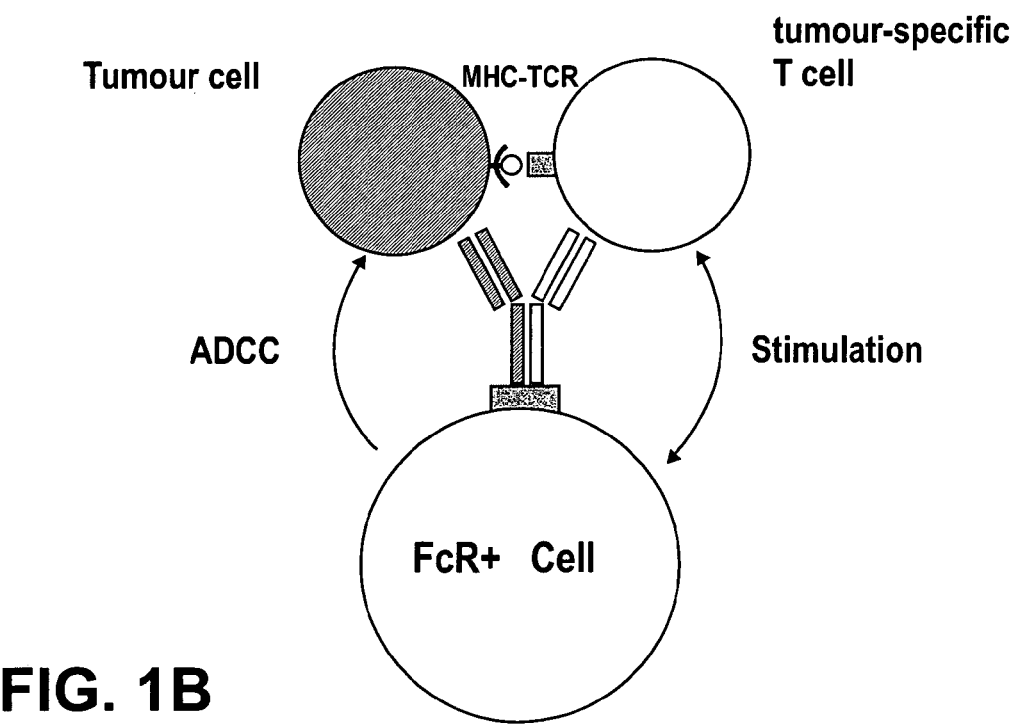

While the intact bsab at the same time binds to and activates the T cell via one of its binding arms (e.g. to CD3 or CD2), co-stimulatory signals derived from the Fc receptor-positive cell bound to the Fc portion of the bsab may be transferred to the T cell. I.e. only the combination of T cell activation via one binding arm of the bsab and the concomitant transfer of co-stimulatory signals from the Fc receptor-positive cell to the T cell results in an effective T cell activation (FIG. 1A). Tumor-specific T cells which have been insufficiently activated at the tumor cell and are anergic may also be reactivated according to the ex vivo pretreatment of the invention (FIG. 1B).

A further important aspect in the induction of anti-tumor immunity is the possibility of phagocytosis, processing and presentation of tumor components by accessory cells (monocytes/macrophages, dendritic cells, and NK—"natural killer"—cells) which have been directed and activated by the bsab. By this classical mechanism of antigen presentation tumor-specific CD4 cells as well as CD8 positive cells can be generated. Moreover, tumor-specific CD4 cells play an important role in the induction of a humoral immune reaction in the context of the T-B cell cooperation.

Bispecific and trispecific antibodies are able to bind to the T cell receptor complex of the T cell by one binding arm and to tumor-associated antigens on the tumor cells by the second binding arm. Thereby, they activate T cells which destroy the tumor cells by releasing cytokines or apoptosis-mediating mechanisms. Furthermore, in the context of their activation by bispecific antibodies it is clearly possible for T cells to recognize tumor-specific antigens via their receptor whereby a long-lasting immunization is initiated (FIG. 1B). In this respect, the intact Fc portion of the bi-specific or trispecific antibody is of particular importance mediating the binding to accessory cells such as monocytes/-macrophages and dendritic cells and inducing these cells to become themselves cytotoxic and/or simultaneously transfer important co-stimulatory signals to the T cell (FIG. 1B). In this manner, it seems to be possible that a T cell reaction may be induced also against so far unknown tumor-specific peptides.

Redirection of possibly anergized tumor-specific T cells to tumor cells by means of bispecific and/or trispecific antibodies and concomitant co-stimulation of such T cells by accessory cells bound to the Fc portion of the bispecific or trispecific antibody might act to reverse the anergy of cytotoxic T cells (CTLs). I.e. using intact heterologous bispecific and/or trispecific antibodies a T cell tolerance existing in the patient against the tumor may be neutralized and, thereby, a long-lasting anti-tumor immunity may be induced.

The last aspect is supported by preliminary in vivo data from experiments with mice indicating a long-lasting anti-tumor immunity following treatment with a syngeneic tumor and intact bsab. In these experiments a total of 14 out of 14 animals which could be successfully treated with bsab after a first tumor injection survived another tumor injection 144 days after the first one—without further administration of bsab (see Example 2).

Further advantages in the ex vivo immunization by bispecific and/or trispecific antibodies are (i) minimizing possible side effects, (ii) controlled binding of the tumor binding arm to the tumor cells outside of the body, and (iii) use of as little bispecific and trispecific antibodies as possible. Principally, there are two different ways of proceeding which will be detailed in the following. An important aspect with long-term incubation is that the bispecific or trispecific antibody employed is exhausted and degraded during the incubation period planned. In this way, this immunization would avoid the lengthy drug approval process.

In the short-term and long-term incubation procedures, the tumor cells are incubated with antibodies over a period of 10 minutes to 5 hours, preferably up to 3 hours, further preferred up to 2 hours and still further preferred 15 minutes to 1 hour. Preferably, the incubation is carried out at a temperature of 4° C. to 25° C., particularly preferred 4° C. to 10° C. The incubation is preferably performed in a sterile environment in buffered saline having a neutral pH. In the case of short-term incubation, reinfusion into the patient is performed immediately afterwards. In the long-term incubation procedure, following this preincubation mononucleated peripheral blood cells are added and incubated together with the preincubated tumor cells/antibodies for a further period of 1 to 14 days, more preferably 3 to 10 days, further preferred 6 to 10 days. Preferably, this incubation is performed at 37° C. under sterile conditions as well as under GMP conditions (Good Manufacturing Production=GMP) in an incubator. As detailed above, in long-term incubation the blood cells may alternatively be incubated together with tumor cells and antibodies under suitable conditions.

The incubation conditions described above are only intended to be an example. Depending on the tumor cells and the antibodies used also other time periods, temperature conditions etc., and in general different incubation conditions may be used. By simple experimentation, the skilled artisan will be able to establish such conditions.

During preincubation the tumor cells are preferably employed in an amount of $10^7$ to $10^9$ cells, further preferred in an amount of about $10^8$ cells. The peripheral blood mononucleated cells are added in an amount of about $10^8$ to $10^{10}$ cells. Naturally, the skilled artisan may select different incubation conditions which may be determined by laboratory experimentation (for example changes in cell number and incubation period). The bispecific and/or trispecific antibodies used in the method of the present invention are added in an amount of 2 to 100 μg, more preferably 5 to 70 g, particularly preferred 5 to 50 μg.

The autologous tumor cells employed are for example irradiated to prevent further survival of tumor cells. For example, gamma radiation is used e.g. employed in a radiation dose of 50 to 100 Gy. In another embodiment of the present invention the autologous tumor cells are treated by chemical substances, for instance by mitomycin C to prevent their further survival.

The antibodies used according to the invention are preferably able to reactivate tumor-specific T cells being in an anergic state. Further, they are able to induce tumor-reactive complement-binding antibodies and thereby a humoral immune reaction.

Binding preferably takes place via CD3, CD2, CD4, CD5, CD6, CD8, CD28, and/or CD44 to the T cell. Fc receptor-positive cells at least bear a Fcγ receptor I, II, or III.

Antibodies which may be employed according to the invention are able to bind to monocytes, macrophages, dendritic cells, "natural killer" cells (NK cells) and/or activated neutrophils being Fcγ receptor 1-positive cells.

The antibodies which may be used according to the invention lead to an induction or increase in the expression of CD40, CD80, CD86, ICAM-1, and/or LFA-3 as co-stimulatory antigens and/or cytokine secretion by the Fc receptor-positive cell. The cytokines preferably are IL-1, IL-2, IL-4, IL-6, IL-8, IL-12, and/or TNF-α.

Binding to the T cell preferably takes place via the T cell receptor complex of the T cell.

The bispecific antibodies which may be used according to the invention preferably are:
  an anti-CD3 X anti-tumor-associated antigen antibody
  and/or anti-CD4 X anti-tumor-associated antigen antibody and/or anti-CD5 X anti-tumor-associated antigen antibody
  and/or anti-CD6 X anti-tumor-associated antigen antibody
  and/or anti-CD8 X anti-tumor-associated antigen antibody
  and/or anti-CD2 X anti-tumor-associated antigen antibody
  and/or anti-CD28 X anti-tumor-associated antigen antibody
  and/or anti-CD44 X anti-tumor-associated antigen antibody.

The trispecific antibodies which may be employed according to the invention preferably are:
  an anti-CD3 X anti-tumor-associated antigen antibody
  and/or anti-CD4 X anti-tumor-associated antigen antibody
  and/or anti-CD5 X anti-tumor-associated antigen antibody
  and/or anti-CD6 X anti-tumor-associated antigen antibody
  and/or anti-CD8 X anti-tumor-associated antigen antibody
  and/or anti-CD2 X anti-tumor-associated antigen antibody
  and/or anti-CD28 X anti-tumor-associated antigen antibody
  and/or anti-CD44 X anti-tumor-associated antigen antibody.

The trispecific antibodies useful according to the invention at least have a T cell binding arm, a tumor cell binding arm and a binding arm which binds to Fc receptor positive cells. The latter of the binding arms mentioned may be an anti-Fc receptor binding arm or a mannose receptor binding arm.

The bispecific antibody preferably is a heterologous intact rat/mouse bispecific antibody.

By the bispecific and trispecific antibodies useful according to the invention T cells are activated and redirected against the tumor cells. Heterologous intact bispecific antibodies which may be preferably used are selected from one or more of the following isotype combinations:

rat-IgG2b/mouse-IgG2a,
rat-IgG2 b/mouse-IgG2b,
rat-IgG2b/mouse-IgG3;
rat-IgG2b/human-IgG1,
rat-IgG2b/human-IgG2,
rat-IgG2b/human-IgG3[oriental allotype G3m(st)=binding to protein A],
rat-IgG2b/human-IgG4;
rat-IgG2b/rat-IgG2c;
mouse-IgG2a/human-IgG3[caucasian allotypes G3m(b+g)=no binding to protein A, in the following indicated as *]
mouse-IgG2a/mouse-[VH-CH1,VL-CL]-human-IgG1-[hinge]-human-IgG3*-[CH2-CH3)
mouse-IgG2a/rat-[VH-CH1,VL-CL]-human-IgG1-[hinge]-human-IgG3*-[CH2-CH3]
mouse-IgG2a/human-[VH-CH1,VL-CL]-human-IgG1-[hinge]-human-IgG3*-[CH2-CH3]
mouse-[VH-CH1, VL-CL]-human-IgG1/rat-[VH-CH1,VL-CL]-human-IgG1-[hinge]human-IgG3*-[CH2-CH3]
mouse-[VH-CH1,VL-CL]-human-IgG4/rat-[VH-CH1,VL-CL]-human-IgG4-[hinge]-human-IgG4[N-terminal region of CH2]-human-IgG3*[C-terminal region of CH2: >aa position 251]-human-IgG3*[CH3]
rat-IgG2b/mouse-[VH-CH1,VL-CL]-human-IgG1-[hinge-CH2-CH3]
rat-IgG2b/mouse-[VH-CH1,VL-CL]-human-IgG2-[hinge-CH2-CH3]
rat-IgG2b/mouse-(VH-CH1,VL-CL]-human-IgG3-[hinge-CH2-CH3, oriental allotype]
rat-IgG2b/mouse-[VH-CH1,VL-CL]-human-IgG4-[hinge-CH2-CH3]
human-IgG1/human-[VH-CH1,VL-CL]-human-IgG1-[hinge]-human-IgG3*-[CH2-CH3]
human-IgG1/rat-[VH-CH1,VL-CL]-human-IgG1-[hinge]-human-IgG4[N-terminal region of CH2]-human-IgG3*[C-terminal region of CH2: >aa position 251]-human-IgG3*[CH3]
human-IgG1/mouse-[VH-CH1,VL-CL]-human-IgG1-[hinge]-human-IgG4[N-terminal region of CH2]-human-IgG3*[C-terminal region of CH2: >aa position 251]-human-IgG3*[CH3] human-IgG1/rat-[VH-CH1,VL-CL]-human-IgG1-[hinge]-human-IgG2[N-terminal region of CH2]-human-IgG3*[C-terminal region of CH2: >aa position 251]-human-IgG3*[CH3]
human-IgG1/mouse-[VH-CH1,VL-CL]-human-IgG1-[hinge]-human-IgG2[N-terminal region of CH2]-human-IgG3*[C-terminal region of CH2: >aa position 251]-human-IgG3*[CH3]
human-IgG1/rat-[VH-CH1,VL-CL]-human-IgG1-[hinge]-human-IgG3*-[CH2-CH3]
human-IgG1/mouse-[VH-CH1,VL-CL]-human-IgG1-[hinge]-human-IgG3*-[CH2-CH3]
human-IgG2/human-[VH-CH1,VL-CL]-human-IgG2-[hinge]-human-IgG3*-[CH2-CH3]
human-IgG4/human-[VH-CH1,VL-CL]-human-IgG4-[hinge]-human-IgG3*-[CH2-CH3]
human-IgG4/human-[VH-CH1,VL-CL]-human-IgG4-[hinge]-human-IgG4[N-terminal region of CH2]-human-IgG3*[C-terminal region of CH2: >aa position 251]-human-IgG3*[CH3]
mouse-IgG2b/rat-[VH-CH1,VL-CL]-human-IgG1-[hinge]-human-IgG3*-[CH2-CH3]
mouse-IgG2b/human-[VH-CH1,VL-CL]-human-IgG1-[hinge]-human-IgG3*-[CH2-CH3]
mouse-IgG2b/mouse-[VH-CH1,VL-CL]-human-IgG1-[hinge]-human-IgG3*-[CH2-CH3]
mouse-[VH-CH1,VL-CL]-human-IgG4/rat-[VH-CH1,VL-CL]-human-IgG4-[hinge]-human-IgG4-[CH2]-human-IgG3*-[CH3]
human-IgG1/rat-[VH-CH1,VL-CL]-human-IgG1-[hinge]-human-IgG4-[CH2]-human-IgG3*-[CH3]
human-IgG1/mouse-[VH-CH1,VL-CL]-human-IgG1-[hinge]-human-IgG4-[CH2]-human-IgG3*-[CH3]
human-IgG4/human-[VH-CH1,VL-CL]-human-IgG4-[hinge]-human-IgG4-[CH2]-human-IgG3*-[CH3]

The antibodies useful according to the invention preferably are monoclonal, chimeric, recombinant, synthetic, semi-synthetic or chemically modified intact antibodies having for example Fv, Fab, scFv or F(ab)$_2$ fragments.

Preferably used are antibodies or derivatives or fragments of human origin or antibodies altered in a way that makes them suitable for application to humans (so-called "humanized antibodies") (see for example Shalaby et al., *J. Exp. Med.* 175 (1992), 217; Mocikat et al., *Transplantation* 57 (1994), 405).

The preparation of the various types of antibodies and fragments mentioned above is obvious to one skilled in the art. The preparation of monoclonal antibodies preferably originating from mammals, e.g. humans, rat, mouse, rabbit or goat, may be performed using conventional methods, as for example described in Köhler and Milstein (*Nature* 256 (1975), 495), in Harlow and Lane (*Antibodies, A Laboratory Manual* (1988), Cold Spring Harbour) or in Galfré (*Meth. Enzymol.* 73 (1981), 3).

Furthermore, it is possible to prepare the antibodies described by means of recombinant DNA technology according to techniques obvious to the skilled artisan (see Kurucz et al., *J. Immunol.* 154 (1995), 4576; Hollinger et al., *Proc. Natl. Acad. Sc. USA* 90 (1993), 6444).

The antibodies used in the present method can be designed and manufactured by a person skilled in the art without undue burden. The enclosed list of references, particularly references (7) to (11) describe methods on how to obtain bispecific and trispecific antibodies to be used in the present invention.

Particularly document (9) of Greenwood et al. discloses the exchange of single immunoglobulin domains (for instance CH2) by suitable cloning technique. By using these cloning technique novel antibody combinations having isotype combinations of the above described heterologous intact bispecific antibodies can be provided. Examples are: human-(VH-CH1, VL-CL)-human IgG4-(hinge)-human IgG4 (N-terminal region of CH2)-human IgG3*(C-terminal region of CH2:>aminoacid position 251)-human IgG3* (CH3).

The combination with an antibody: human IgG4 for the preparation of the bispecific antibody: human IgG4/human-(VH-CH1, VL-CL)-human IgG4-(hinge)-human IgG4 (N-terminal region of CH2)-human IgG3*(C-terminal region of CH2:>aminoacid position 251)-human IgG3* (CH3) is prepared by simple cell fusion as described for instance in document (6).

On the one hand, the preparation of antibodies having two different specificities, the so-called bispecific antibodies, may be performed using recombinant DNA technology, but on the other hand also by the so-called hybrid-hydridoma fusion technique (see for example Milstein et al., *Nature* 305

(1983), 537). By this technique, hybridoma cell lines producing antibodies each having one of the desired specificities are fused, and recombinant cell lines producing antibodies with both specificities are identified and isolated.

The problem underlying the invention may be solved both by bispecific and by trispecific antibodies insofar as they bind to a T cell, bind to at least one antigen on a tumor cell, and in the case of bispecific antibodies, bind by their Fc portion to Fc receptor-positive cells, or in the case of trispecific antibodies, bind by a third specificity to Fc receptor-positive cells. In the following, the preparation of antibodies having two and three specificities is described in more detail. To provide such bispecific and trispecific antibodies belongs to the state of the art, and the literature describing such methods of preparation is hereby incorporated by reference in its entirety.

The preparation of antibodies having three specificities, so-called trispecific antibodies, which are also suitable to solve the fundamental problem of the invention may be for example carried out by coupling to one of the heavy IgG chains of a bispecific antibody a third antigen-binding site having another specificity, e.g. in the form of "single chain variable fragments" (scFv). The scFv may be for example bound to one of the heavy chains via a -S-S($G_4S$)$_n$D-I linker (S=serine, G=glycine, D=aspartate, I=isoleucine).

Figure 5:
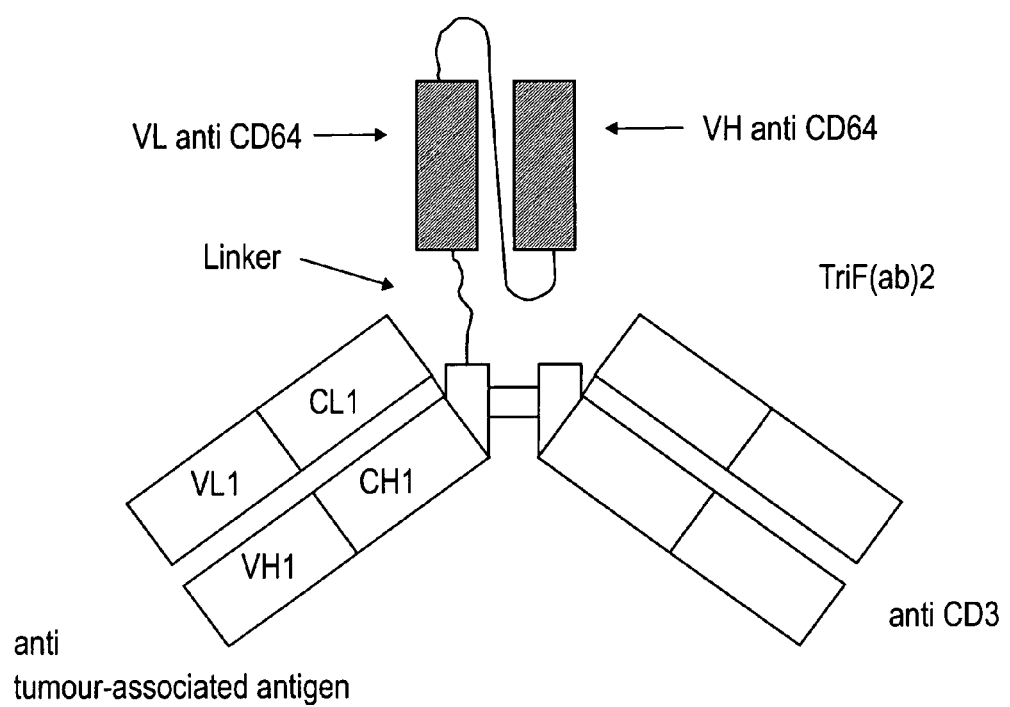

Analogously, trispecific F(ab)$_2$ constructs may be prepared substituting the CH2-CH3 regions of the heavy chain of one specificity of a bispecific antibody by a scFv of a third specificity while the CH2-CH3 regions of the heavy chain of the other specificity are removed, e.g. by introduction of a stop codon (at the end of the "hinge" region) into the coding gene for example by homologous recombination (see FIG. 5).

Figure 6:
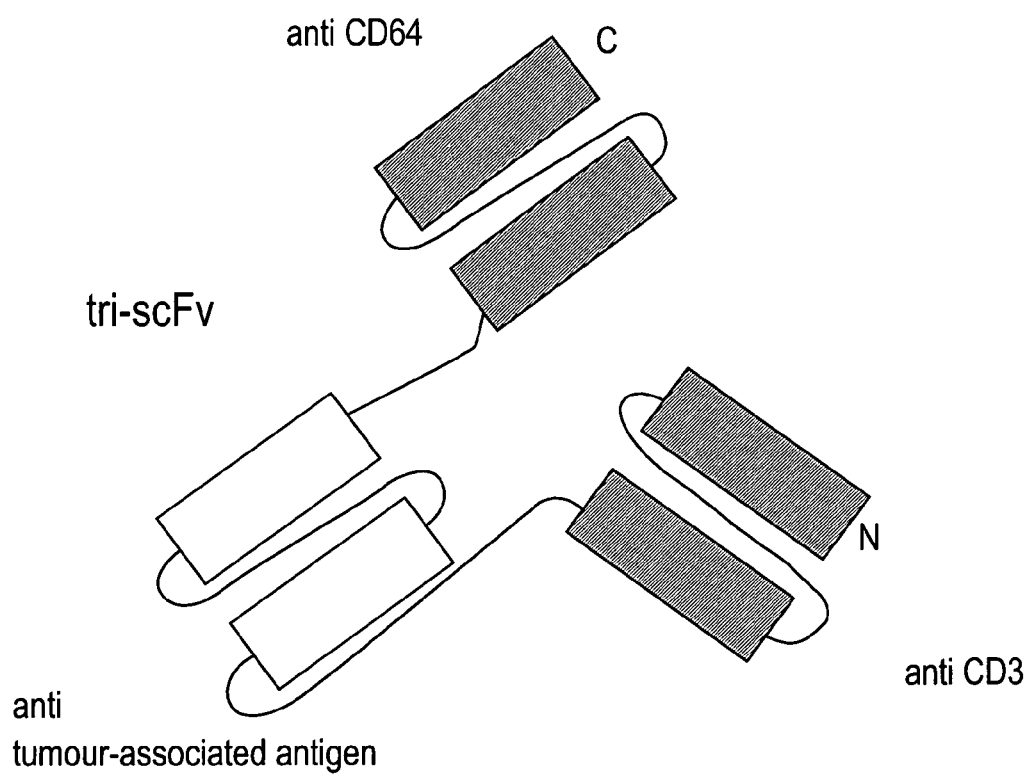

It is also possible to prepare trispecific scFv constructs. In this case three VH-VL regions representing three different specificities are arranged in series (FIG. 6).

According to the invention, there are for example used intact bispecific antibodies. Intact bispecific antibodies are a combination of two antibody semi-molecules (each of one H and L immunoglobulin chain) each representing one specificity and, like normal antibodies, having in addition a Fc portion which performs the well known effector functions. Preferably, they are prepared by quadroma technology. This method of preparation is described representatively in DE-A-44 19 399. This document is incorporated by reference in its entirety for the purpose of complete disclosure also with respect to a definition of bispecific antibodies. Naturally, also other methods of preparation may be employed as long as they result in the intact bispecific antibodies defined above required according to the invention.

For example, by a newly developed method of production (6) intact bispecific antibodies may be prepared in a sufficient amount. The combination of 2 bispecific antibodies against 2 different tumor-associated antigens (e.g. c-erb-B2, ep-cam, such as GA-733-2=C215) on the mamma carcinoma cells minimizes the risk that tumor cells expressing only one antigen are not recognized.

There have also been attempts to achieve an anti-tumor immunity by treatment with bispecific F(ab')2 fragments having the specificities of anti-c-erb-B2 x anti CD64. The main disadvantage of bsF(ab')2 fragments is that due to the specificities used only FcγRI+ cells are redirected to the tumor. T cells are not redirected to the tumor by this bispecific antibody. While bsF(ab')2 fragments have the potential to directly destroy the tumor, they are unable to establish an anti-tumor immunity themselves. Only the T cell with its specific T cell receptor has this capability. While the FcγRI+ cells are able to indirectly activate tumor-specific T cells by presenting tumor-specific peptides (via MHCI or MHCII, respectively), for example following phagocytosis of tumor components, the efficiency of induction of an anti-tumor immunity is this case is not as high (only in 30% of the patients).

Further advantages of intact bsabs capable of redirecting T cells as compared to the above-mentioned bsF(ab')2 fragments are detailed in the following:

1. To intact bsabs there may bind Fc receptor-positive cells and may on the one hand by ADCC (antibody-dependent cell-mediated cytotoxicity) contribute directly to the destruction of the tumor and on the other hand to T cell activation, as detailed above.

2. By intact T cell-redirecting bsabs also anergized tumor-specific T cells are directed to the tumor cell which according to the invention may be directly reactivated at the tumor. This may not be achieved using a bsF(ab')2 fragment having the specificities of anti CD64 x anti tumor-associated antigen.

3. A bsF(ab')2 fragment having the specificities of anti CD64 x anti tumor-associated antigen is merely capable of achieving an anti-tumor immunity in 30% of the patients while according to the invention in experiments with mice using T cell-redirecting intact bsabs a protection in 100% of the animals could be achieved.

Binding of the bsabs to Fcγ-RI has two significant advantages with respect to optimum anti-tumor effectivity:

(1) Fcγ-RI-positive cells are capable of eliminating tumor cells by means of ADCC(11) and in this respect may contribute synergistically to the anti-tumor-effect of the cytotoxic T cells which have been directed to the tumor cell by the bsab (13).

(2) Fcγ-RI-positive cells (such as monocytes/macrophages/dendrites) are capable of providing important co-stimulatory signals similar to antigen presentation to the T cell and thereby to prevent anergizing of the T cell. Furthermore, as shown in FIG. 1, as a desired side product due to the intact bsab-mediated interaction of the T cell with accessory cell and tumor cell there may be stimulated T cells having a T cell receptor which recognizes tumor-specific peptides (presented on the tumor cell via MHC antigens). The co-stimuli necessary for a correct activation of the T cell in this situation would be provided by the accessory cell (e.g. the monocyte). In this respect, the antibody of the invention besides the direct T cell receptor-independent bsab-mediated tumor destruction (FIG. 1A) should also activate and generate tumor-specific T cells (FIG. 1B) which after degradation of the bsabs continue to patrol in the patient. I.e. by means of intact bsabs similar to gene therapeutical approaches (e.g. by incorporation of co-stimulatory antigens such as B-7 into the tumor cell) the tumor tolerance in the patient may be overcome.

In this respect, it is further beneficial that the expression of Fcγ-RI is up-regulated on the respective cells following G-CSF treatment.

The invention has been described in the above and will be described in the following in particular with respect to bispecific antibodies. Instead of bispecific antibody, of course also trispecific antibodies may be used as long as they comply with the provisions made.

Figure 2:
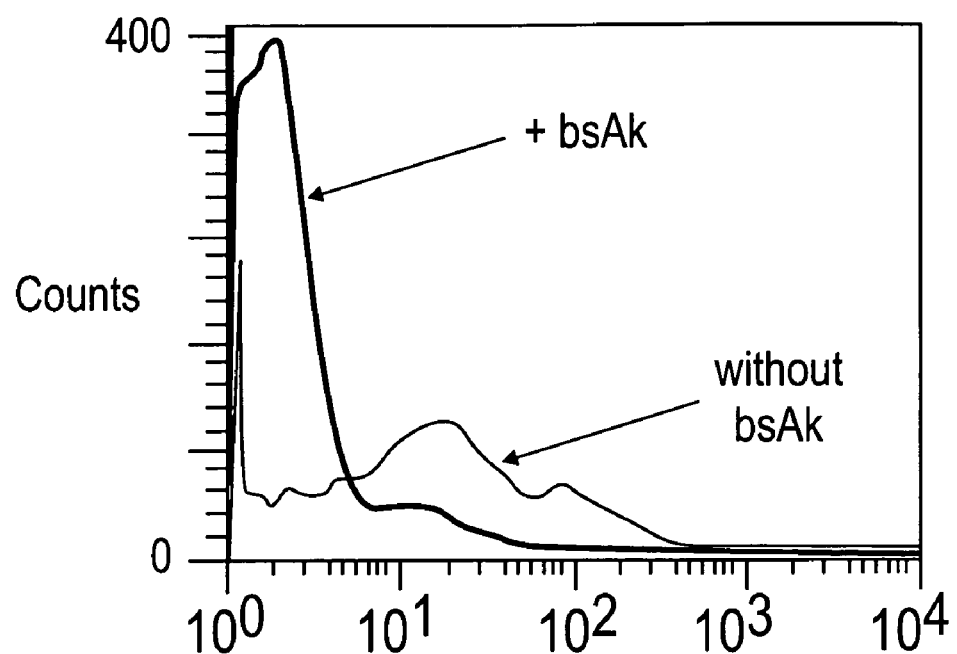
Figure 3:
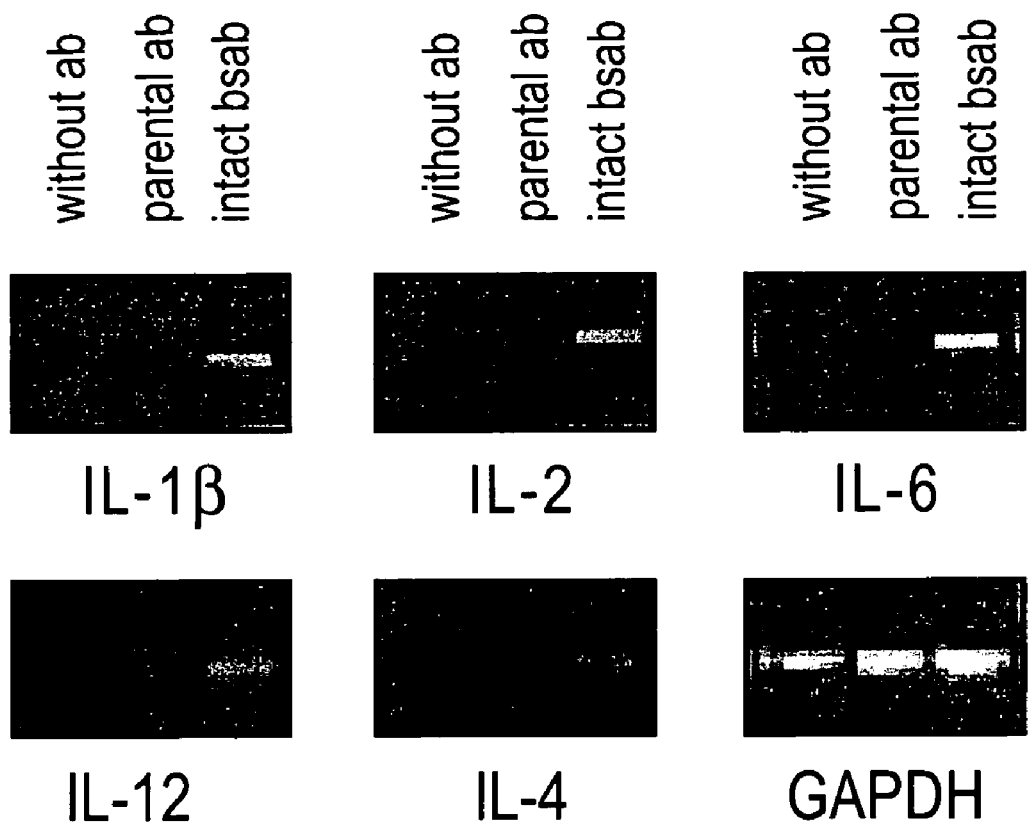
Figure 4A:
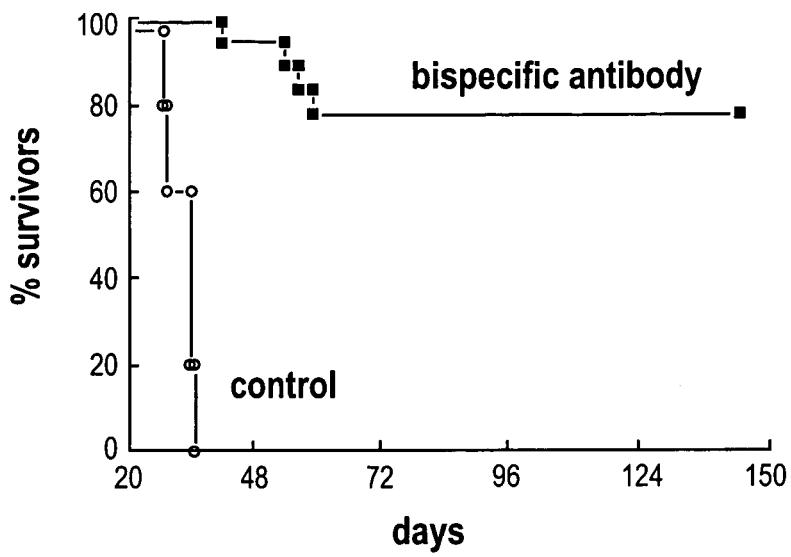
Figure 4B:
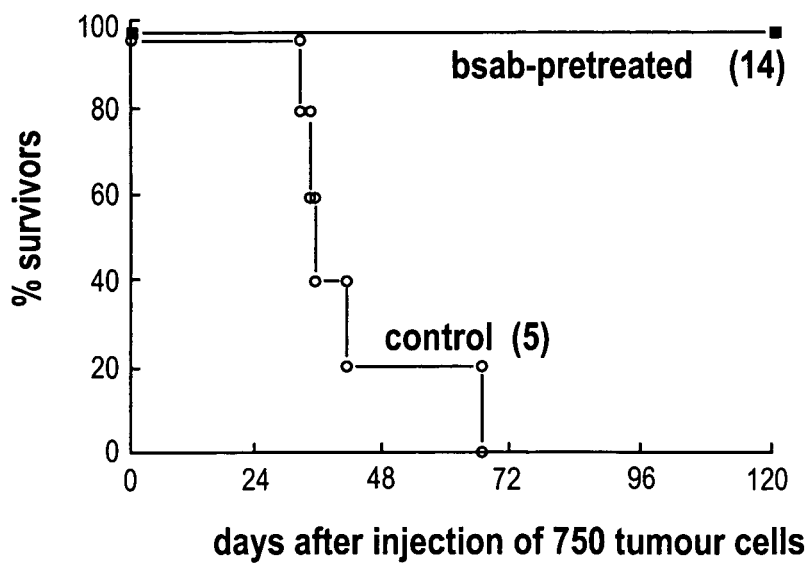

The invention has been and will be described with respect to the accompanying Figures. The Figures show:

FIG. 1: the role of accessory cells in tumor immunotherapy by means of bispecific antibodies;

FIG. 2: the destruction of tumor cells following administration of bispecific antibodies as evidenced by flow-cytometry;

FIG. 3: induction of cytokines by intact bispecific antibodies only but not by parental antibodies;

FIG. 4: efficiency of the method according to the invention in vivo;

FIG. 5: trispecific F(ab)$_2$ antibodies;

FIG. 6: trispecific scFv antibody.

IMMUNIZATION PROTOCOLS

Ex Vivo Immunization (Short-Term Incubation)

1. Preparation of a single cell suspension ($10^7$–$10^9$ cells) from autologous tumor material (or allogenic tumor cells of the same tumor type) with subsequent γ irradiation (50–100 Gy).

2. Addition of bsabs (5–50 μg) and incubation for 45 minutes at 4° C. Afterwards washing away of unbound antibodies.

3. Reinfusion of the cell mixture (i.v.).

Ex Vivo Immunization (Long-Term Incubation)

1. Preparation of a single cell suspension ($10^7$–$10^9$ cells) from autologous tumor material (or allogenic tumor cells of the same tumor type) with subsequent γ irradiation (50–100 Gy).

2. Addition of bsabs (5–50 μg), 45 minutes incubation.

3. Addition of PBMCs ($10^8$–$10^{10}$), [alternatively: $1×10^9$ cells obtained from T cell aphaeresis].

4. After 5 to 7 days monitoring of T cell reactivity by transfer of aliquots e.g. to allogenic breast cancer cell lines (MCF-7, MX-1).

5. Reinfusion (i.v.) of the cultured PBMCs on days 4 to 14 into the patient (in the case of T cell aphaeresis: cryo conservation).

Abbreviations: PBMCs, peripheral blood mononucleated cells; i.v., intravenously.

A similar assay but instead depending on the addition of cytokines and carried out using conventional bsabs (no activation of accessory cells by bsabs of the subclass combination rat IgG2B x rat IgG1) demonstrates the principal effectivity of such an ex vivo immunization in the animal model (5).

In contrast to this, the advantage of the method disclosed herein resides in the "self-sufficiency" with respect to cytokines (such as INF-α or TNF-α) required for an up-regulation of for example MHC 1 on the tumor cell by simultaneous activation of T cells and accessory cells (monocytes/macrophages, FIG. 1, parts A and B) on the tumor cell. This is achieved by the particular subclass combination mentioned at the beginning of the intact bsab used herein. In the case of short-term incubation these processes take place in the patient. Further advantages in short-term incubation are (i) avoiding the cultivation of the cell suspension with serum-containing medium otherwise necessary. (ii) Due to this, also the cost-intensive cultivation according to GMP regulations may be omitted. (iii) A further important aspect is avoidance or reduction, respectively, of possible side effects by the bsab because of the significantly lower amount of antibodies applied.

An advantage in long-term incubation is that the bsab in vitro after some time exhausts itself (and, thus, this method may be established not as a medicament but as a "medical device").

EXAMPLE 1

Bispecific Antibody-Mediated Lysis of Tumor Cells by Allogenic T Cells

H-Lac78 is a cell line which has been established from a hypopharynx carcinoma and which expresses epcam to a high extent (own FRCS data). Using H-Lac78 and peripheral mononucleated cells (PBMC) from volunteers it was possible to detect the generation of allogenic cytotoxic T lymphocytes. For this purpose, constant amounts of H-Lac78 ($2×10^4$) were incubated with varying amounts of PBMCs in the presence (10 ng) or absence of a bsab (anti epcam x anti CD3). After a period of seven days the PBMCs were removed and analyzed in a flow-cytometer. At the same time, the number of H-Lac78 tumor cells was determined. The activation of T cells may be observed microscopically by means of cluster formation; proliferation may be evidenced by the incorporation of radiolabeled thymidine. The detection of remaining tumor cells is performed microscopically as well as by the epithelial marker epcam which is not expressed on peripheral blood cells. As shown in FIG. 2, the H-Lac78 cells were completely lysed in the presence of bsab, i.e. no epcam-positive cells were detectable in the flow-cytometer after seven days. These data were confirmed by microscopic observations. In contrast, without bsab a confluent layer of H-Lac78 cells was observed in the wells and epcam-positive cells were detectable by FACS.

Detection of Activated Allospecific CTLs by Transfer Experiment

In a subsequent transfer experiment the PBMCs incubated with or without bsab, respectively, were transferred onto new H-Lac78 cells without readdition of bsab. Also in this case, the tumor cells were lysed but exclusively by PBMCs which had been activated by bsab previously. H-Lac78 lysis was complete within 24 hours up to a ratio of 2 PBMCs to 1 H-Lac78 cell. This result indicates the generation of allospecific CTLs without external addition of interleukin-2 (IL-2). Since IL-2 is essential for the activation of T lymphocytes, the data obtained herein suggest that by bsab-mediated activation IL-2 is produced by the T cells themselves. Induction of IL-2 mRNA by addition of bsab could be confirmed afterwards by RT-PCR where the bsab was clearly superior to the parental starting antibodies (FIG. 3). This observation is important insofar as IL-2 has been described as an anti-tumor effective cytokine; but the systemic administration of which in an appropriate concentration is limited because of its toxicity. In contrast, the risk of toxicity does not appear in the local production of IL-2 as it is for example induced by intact bsab. Also, since an effective induction of IL-2 (and IL-12) requires stimulation of T cells via the T cell receptor and CD28, this indicates the importance of Fc receptor-positive cells (providing the ligands for CD28, CD80, and CD86) in T cell activation by intact bsab.

EXAMPLE 2

To address the question whether bispecific antibodies are able to induce a long-lasting anti-tumor immunity C57BL/6 mice were first injected with $5×10^3$ syngeneic B16 tumor cells. Two days later, a group of mice (number of 18) were treated with intact bsab prepared by quadroma technology (6) and recognizing a target structure (ep-cam/C215=tumor-associated antigen) on the tumor cell as well as CD3 on the T cells. A second group (number of 6) received an equimolar amount of Fab fragments of both of the specificities contained in the bsab only. While all of the animals of the Fab control group died or had to be sacrificed within 56 days, 14 of the 18 animals treated with bsab survived. 144 days after the first injection of tumor cells the 14 surviving animals were injected with another dose of 750 B16 tumor cells but this time without administration of bsabs. As a control, the same number of tumor cells was administered to 5 untreated animals. While the last animal of the untreated control group had to be sacrificed 66 days after tumor injection, all of the animals treated with bsab survived (monitoring period: 120 days following second tumor cell injection). See also FIGS. 4A and B: Survival graphs of the two subsequent experiments described above.

REFERENCES

1. Haagen et al., Interaction of human monocyte Fcγ receptors with rat IgG2b, *J. Immunolog.*, 154:1852–1860(1995)
2. Gast G. C., Haagen, I.-A., van Houten A. A., Klein S., Duits A. J., de Weger R. A., Vroom T. M., Clark M. R., J. philips, van Dijk A. J. G, de Lau W. B. M., Bast B. J. E. G, T-cell activation after intravenous administration of CE3 X CD19 bispecific antibody in patients with non-Hodgkin lymphoma. *Cancer Immunol. Immunother.*, 40:390 (1995)
3. Tenny, C., Jacobs, S., Stoller, R., Earle, M., and Kirkwood, J. Adoptive cellulare immunotherapy with high-dose chemotherapy and autologous bone marrow rescue (AMBR) for recurrent breast cancer (meeting abstract). *Proc. Annu. Meet. Am. Soc. Clin. Oncol,* 11:A88 (1992) ISSN: 0736-7589. CO: PMAODO-7589 CO, (1993)
4. Early Breast Cancer Trialists' Collaborative Group, Systemic treatment of early breast cancer by hormonal, cytotoxic, or immune therapy—133 randomised trials involving 31 000 recurrences and 24 000 deaths among 75 000 women. Part II *Lancet* 339:71–85 (1992))
5. Guo et al., effective tumor vaccines generated by in citro modification of tumor cells with cytokines and bispecific monoclonal antibodies. *Nature Medicine,* 3:451 (1997)
6. Lindhofer et al., Preferential species-restricted heavy-light chain pairing in rat-mouse quadromas: Implications for a single step purification of bispecific antibodies, *J. Immunology,* 155:219 (1995)
7. (Bruggemann et al., A MATCHED SET OF RAT/MOUSE CHIMERIC ANTIBODIES: Identification and Biological Properties of RAT H CHAIN CONSTANT REGIONS μ, γ1, γ2a, γ2b, ε, and α$^1$, *J. Immunology,* 142:3145 (1989)
8. Routledge et al., A humanized monovalent CD3 antibody whih can activvate homologous complement, *Eur. J. Immunology,* 21:2717 (1991)
9. Greenwood et al., Structural motifs involved in human IgG antibody effector functions, *Eur. J. Immunology,* 23:1098 (1993);
10. Kardinal et al., Genetic stability of gene targeted immunoglobulin loci. I Heavy chain isotype exchange induced by a universal gene replacement vector, *J. Immunology,* 89:309 (1996);
11. Kardinal et al., Integration vectors for antibody chimerization by homologous recombination in hybridoma cells, *Eur. J. Immunology,* 25:792 (1995))

The invention claimed is:

1. A method for the preparation of an antibody-tumor cell preparation for immunization of humans and animals against tumor cells comprising the steps of:
   a) isolating autologous tumor cells;
   b) treating the tumor cells to prevent the survival thereof following reinfusion;
   c) incubating the thus treated tumor cells with intact heterologous bispecific antibodies showing the following properties:
      (i) binding to a T cell;
      (ii) binding to at least one tumor-associated antigen on a tumor cell;
      (iii) binding, by their Fc portion to Fc receptor-positive cells; and
      (iv) capable of activating the Fc receptor-positive cell whereby the expression of cytokines, co-stimulatory antigens or both is induced or increased,
   wherein the bispecific antibodies have isotype combinations selected from the group consisting of:
      rat-IgG2b/human-IgG1,
      rat-IgG2b/human-IgG2,
      rat-IgG2b/human-IgG3[oriental allotype G3m(st)=binding to protein A],
      rat-IgG2b/human-IgG4,
      rat-IgG2b/rat-IgG2c,
      mouse-IgG2a/human-IgG3[caucasian allotypes G3m(b+g)=no binding to protein A, in the following indicated as *],
      mouse-IgG2a/mouse-[VH-CH1,VL-CL]-human-IgG1-[hinge]-human-IgG3*-[CH2-CH3],
      mouse-IgG2a/rat-[VH-CH1,VL-CL]-human-IgG1-[hinge]-human-IgG3*-[CH2-CH3],
      mouse-IgG2a/human-[VH-CH1,VL-CL]-human-IgG1-[hinge]-human-IgG3*-[CH2-CH3],
      mouse-[VH-CH1,VL-CL]-human-IgG1/rat-[VH-CH1,VL-CL]-human-IgG1-[hinge]-human-IgG3*-[CH2-CH3],
      mouse-[VH-CH1,VL-CL]-human-IgG4/rat-[VH-CH1,VL-CL]-human-IgG4-[hinge]-human-IgG4[N-terminal region of CH2]-human-IgG3*[C-terminal region of CH2: >aa position 251]-human-IgG3*[CH3],
      rat-IgG2b/mouse-[VH-CH1,VL-CL]-human-IgG1-[hinge-CH2-CH3],
      rat-IgG2b/mouse-[VH-CH1,VL-CL]-human-IgG2-[hinge-CH2-CH3],
      rat-IgG2b/mouse-[VH-CH1,VL-CL]-human-IgG3-[hinge-CH2-CH3, oriental allotype],
      rat-IgG2b/mouse-[VH-CH1,VL-CL]-human-IgG4-[hinge-CH2-CH3],
      human-IgG1/human-[VH-CH1,VL-CL]-human-IgG1-[hinge]-human-IgG3*-[CH2-CH3],
      human-IgG1/rat-[VH-CH1,VL-CL]-human-IgG1-[hinge]-human-IgG4[N-terminal region of CH2]-human-IgG3*[C-terminal region of CH2: >aa position 251]-human-IgG3*[CH3],
      human-IgG1/mouse-[VH-CH1,VL-CL]-human-IgG1-[hinge]-human-IgG4[N-terminal region of CH2]-human-IgG3*[C-terminal region of CH2: >aa position 251]-human-IgG3*[CH3],
      human-IgG1/rat-[VH-CH1,VL-CL]-human-IgG1-[hinge]-human-IgG2 [N-terminal region of CH2]-human-IgG3*[C-terminal region of CH2: >aa position 251]-human-IgG3*[CH3],
      human-IgG1/mouse-[VH-CH1,VL-CL]-human-IgG1-[hinge]-human-IgG2[N-terminal region of CH2]-human-IgG3*[C-terminal region of CH2: >aa position 251]-human-IgG3*[CH3],
      human-IgG1/rat-[VH-CH1,VL-CL]-human-IgG1-[hinge]-human-IgG3*-[CH2-CH3],
      human-IgG1/mouse-[VH-CH1,VL-CL]-human-IgG1-[hinge]-human-IgG3*-[CH2-CH3],
      human-IgG2/human-[VH-CH1,VL-CL]-human-IgG2-[hinge]-human-IgG3*-[CH2-CH3], human-IgG4/human-[VH-CH1,VL-CL]-human-IgG4-
[hinge]-human-IgG3*-[CH2-CH3],
human-IgG4/human-[VH-CH1,VL-CL]-human-IgG4-
[hinge]-human-IgG4[N-terminal region of CH2]-human-IgG3*[C-terminal region of CH2: >aa position 251]-human-IgG3*[CH3],
mouse-IgG2b/rat-[VH-CH1,VL-CL]-human-IgG1-
[hinge]-human-IgG3*-[CH2-CH3],
mouse-IgG2b/human-[VH-CH1,VL-CL]-human-IgG1-
[hinge]-human-IgG3*-[CH2-CH3],
mouse-IgG2b/mouse-[VH-CH1,VL-CL]-human-IgG1-
[hinge]-human-IgG3*-[CH2-CH3],
mouse-[VH-CH1,VL-CL]-human-IgG4/rat-[VH-CH1,
VL-CL]-human-IgG4-[hinge]-human-IgG4-[CH2]-human-IgG3*-[CH3],
human-IgG1/rat-[VH-CH1,VL-CL]-human-IgG1-
[hinge]-human-IgG4-[CH2]-human-IgG3*-[CH3],
human-IgG1/mouse-[VH-CH1,VL-CL]-human-IgG1-
[hinge]-human-IgG4-[CH2]-human-IgG3*-[CH3],
human-IgG4/human-[VH-CH1,VL-CL]-human-IgG4-
[hinge]-human-IgG4-[CH2]-human-IgG3*-[CH3],
rat-IgG2b/mouse-IgG2a,
rat-IgG2b/mouse-IgG2b, and
rat-IgG2b/mouse-IgG3.

2. The method according to claim 1, in which said antibodies bind Fc receptor-positive cells having a Fcγ receptor I, II, or III.

3. The method according to claim 2, in which said Fcγ receptor I-positive cells are selected from the group consisting of monocytes, macrophages, dendritic cells, and activated neutrophils.

4. The method according to claim 1, in which said antibodies induce tumor-reactive complement-binding antibodies, thereby inducing a humoral immune response.

5. The method according to claim 1, in which said antibodies bind to the T cells via CD2, CD3, CD4, CD5, CD6, CD8, CD28 or CD44.

6. The method according to claim 1, in which said antibodies, following their binding to the Fc receptor-positive cells, initiate or increase the expression of co-stimulatory antigens CD40, CD80, CD86, ICAM-1 and/or LFA-3 and/or initiate or increase the secretion of cytokines by the Fc receptor-positive cells.

7. The method according to claim 1, in which said antibodies increase the secretion of IL-1, IL-2, IL-4, IL-6, IL-8, IL-12 or TNF-α or a combination thereof.

8. The method according to claim 1, in which said bispecific antibody is an anti-CD3 X anti-tumor-associated antigen antibody or anti-CD4 X anti-tumor-associated antigen antibody or anti-CD5 X anti-tumor-associated antigen antibody or anti-CD6 X anti-tumor-associated antigen antibody or anti-CD8 X anti-tumor-associated antigen antibody or anti-CD2 X anti-tumor-associated antigen antibody or anti-CD28 X anti-tumor-associated antigen antibody or anti-CD44 X anti-tumor-associated antigen antibody.

9. The method according to claim 1, in which said tumor cells are incubated with the antibodies for a period of 10 minutes to 5 hours.

10. The method according to claim 1, in which said tumor cells are incubated with the antibodies for a period of 15 minutes to 120 minutes.

11. The method according to claim 1, in which said tumor cells are present in the amount of about $10^7$ to $10^9$ cells.

12. The method according to claim 1, in which said bispecific antibodies are added in an amount of 2 to 100 μg.

13. The method according to claim 1, in which said treating of the tumor cells in step b is performed by irradiation.

14. A method for preparing a vaccine comprising an antibody-tumor cell preparation, said method comprising preparing an antibody-tumor cell preparation by the method of claim 1, and preparing a vaccine from said antibody-tumor cell preparation.

15. A method for preparing a vaccine comprising activated peripheral blood mononucleated cells, said method comprising preparing an antibody-tumor cell preparation by a method comprising steps (a) and (b) of the method of claim 1 and further comprising the step of incubating the thus-treated tumor cells with both intact heterologous bispecific antibodies and peripheral blood mononucleated cells, thereby activating said peripheral blood mononucleated cells, and preparing a vaccine from the thus-activated peripheral blood mononucleated cells, wherein said intact heterologous bispecific antibodies have the following properties:
(i) binding to a T cell;
(ii) binding to at least one tumor-associated antigen on a tumor cell;
(iii) binding by their Fc portion to Fc receptor-positive cells; and
(iv) capable of activating the Fc receptor-positive cell whereby the expression of cytokines, co-stimulatory antigens or both is induced or increased,
and said bispecific antibodies have isotype combinations selected from the group consisting of:
rat-IgG2b/human-IgG1,
rat-IgG2b/human-IgG2,
rat-IgG2b/human-IgG3[oriental allotype G3m(st)=binding to protein A],
rat-IgG2b/human-IgG4,
rat-IgG2b/rat-IgG2c,
mouse-IgG2a/human-IgG3 [caucasian allotypes G3m (b+g)=no binding to protein A, in the following indicated as *],
mouse-IgG2a/mouse-[VH-CH1, VL-CL]-human-IgG1-[hinge]-human-IgG3*-[CH2-CH3],
mouse-IgG2a/rat-[VH-CH1, VL-CL]-human-IgG1-[hinge]-human-IgG3*-[CH2-CH3],
mouse-IgG2a/human-[VH-CH1,VL-CL]-human-IgG1-[hinge]-human-IgG3*-[CH2-CH3],
mouse-[VH-CH1,VL-CL]-human-IgG1/rat-[VH-CH1, VL-CL]-human-IgG1-[hinge]-human-IgG3*-[CH2-CH3],
mouse-[VH-CH1,VL-CL]-human-IgG4/rat-[VH-CH1, VL-CL]-human-IgG4-[hinge]-human-IgG4[N-terminal region of CH2]-human-IgG3*[C-terminal region of CH2: >aa position 251]-human-IgG3* [CH3],
rat-IgG2b/mouse-[VH-CH1,VL-CL]-human-IgG1-[hinge-CH2-CH3],
rat-IgG2b/mouse-[VH-CH1,VL-CL]-human-IgG2-[hinge-CH2-CH3],
rat-IgG2b/mouse-[VH-CH1,VL-CL]-human-IgG3-[hinge-CH2-CH3, oriental allotype],
rat-IgG2b/mouse-[VH-CH1,VL-CL]-human-IgG4-[hinge-CH2-CH3],
human-IgG1/human-[VH-CH1,VL-CL]-human-IgG1-[hinge]-human-IgG3*-[CH2-CH3],
human-IgG1/rat-[VH-CH1,VL-CL]-human-IgG1-[hinge]-human-IgG4[N-terminal region of CH2]-human-IgG3*[C-terminal region of CH2: >aa position 251]-human-IgG3*[CH3], human-IgG1/mouse-[VH-CH1,VL-CL]-human-IgG1-[hinge]-human-IgG4[N-terminal region of CH2]-human-IgG3*[C-terminal region of CH2: >aa position 251]-human-IgG3*[CH3],
human-IgG1/rat-[VH-CH1, VL-CL]-human-IgG1-[hinge]-human-IgG2[N-terminal region of CH2]-human-IgG3*[C-terminal region of CH2: >aa position 251]-human-IgG3*[CH3],
human-IgG1/mouse-[VH-CH1, VL-CL]-human-IgG1-[hinge]-human-IgG2[N-terminal region of CH2]-human-IgG3*[C-terminal region of CH2: >aa position 251]-human-IgG3*[CH3],
human-IgG1/rat-[VH-CH1,VL-CL]-human-IgG1-[hinge]-human-IgG3*-[CH2-CH3],
human-IgG1/mouse-[VH-CH1,VL-CL]-human-IgG1-[hinge]-human-IgG3*-[CH2-CH3],
human-IgG2/human-[VH-CH1, VL-CL]-human-IgG2-[hinge]-human-IgG3*-[CH2-CH3],
human-IgG4/human-[VH-CH1,VL-CL]-human-IgG4-[hinge]-human-IgG3*-[CH2-CH3],
human-IgG4/human-[VH-CH1,VL-CL]-human-IgG4-[hinge]-human-IgG4[N-terminal region of CH2]-human-IgG3*[C-terminal region of CH2: >aa position 251]-human-IgG3*[CH3],
mouse-IgG2b/rat-[VH-CH1, VL-CL]-human-IgG1-[hinge]-human-IgG3*-[CH2-CH3],
mouse-IgG2b/human-[VH-CH1, VL-CL]-human-IgG1-[hinge]-human-IgG3*-[CH2-CH3],
mouse-IgG2b/mouse-[VH-CH1, VL-CL]-human-IgG1-[hinge]-human-IgG3*-[CH2-CH3],
mouse-[VH-CH1,VL-CL]-human-IgG4/rat-[VH-CH1, VL-CL]-human-IgG4-[hinge]-human-IgG4-[CH2]-human-IgG3*-[CH3],
human-IgG1/rat-[VH-CH1, VL-CL]-human-IgG1-[hinge]-human-IgG4-[CH2]-human-IgG3*-[CH3],
human-IgG1/mouse-[VH-CH1, VL-CL]-human-IgG1-[hinge]-human-IgG4-[CH2]-human-IgG3*-[CH3],
human-IgG4/human-[VH-CH1,VL-CL]-human-IgG4-[hinge]-human-IgG4-[CH2]-human-IgG3*-[CH3],
rat-IgG2b/mouse-IgG2a,
rat-IgG2b/mouse-IgG2b, and
rat-IgG2b/mouse-IgG3.

16. The method according to claim 15 in which said incubation of step (d) is performed for a period of 1 to 14 days.

17. The method according to claim 15 in which said incubation of step (d) is performed with about $10^8$ to $10^{10}$ mononucleated peripheral cells.

18. The method of claim 15, wherein the peripheral blood mononucleated cells are added following a preincubation of the thus-treated tumor cells with said intact heterologous bispecific antibodies.

19. A method for preventing the reoccurrence of a tumor, said method comprising administering an antibody-tumor cell preparation prepared according to the method of claim 1 to an individual in whom tumor cells have reappeared.

20. A pharmaceutical composition comprising an antibody-tumor cell preparation obtained by the method of claim 1.

21. A method for preventing the recurrence of a tumor, said method comprising: preparing an antibody-tumor cell preparation by the method of claim 1 in which step (c) is replaced with step (d), which comprises incubating the thus-treated tumor cells with both intact heterologous bispecific antibodies and peripheral blood mononucleated cells, thereby activating said peripheral blood mononucleated cells; and administering to an individual in whom tumor cells have reappeared the activated peripheral blood mononucleated cells, wherein said intact heterologous bispecific antibodies have the following properties:
(i) binding to a T cell;
(ii) binding to at least one tumor-associated antigen on a tumor cell;
(iii) binding, by their Fc portion to Fc receptor-positive cells; and
(iv) capable of activating the Fc receptor-positive cell whereby the expression of cytokines, co-stimulatory antigens or both is induced or increased,
and said bispecific antibodies have isotype combinations selected from the group consisting of:
rat-IgG2b/human-IgG1,
rat-IgG2b/human-IgG2,
rat-IgG2b/human-IgG3[oriental allotype G3m(st)=binding to protein A],
rat-IgG2b/human-IgG4,
rat-IgG2b/rat-IgG2c,
mouse-IgG2a/human-IgG3[caucasian allotypes G3m(b+g)=no binding to protein A, in the following indicated as *],
mouse-IgG2a/mouse-[VH-CH1,VL-CL]-human-IgG1-[hinge]-human-IgG3*-[CH2-CH3],
mouse-IgG2a/rat-[VH-CH1,VL-CL]-human-IgG1-[hinge]-human-IgG3*-[CH2-CH3]
mouse-IgG2a/human-[VH-CH1,VL-CL]-human-IgG1-[hinge]-human-IgG3*-[CH2-CH3],
mouse-[VH-CH1,VL-CL]-human-IgG1/rat-[VH-CH1, VL-CL]-human-IgG1-[hinge]-human-IgG3*-[CH2-CH3],
mouse-[VH-CH1,VL-CL]-human-IgG4/rat-[VH-CH1, VL-CL]-human-IgG4-[hinge]-human-IgG4[N-terminal region of CH2]-human-IgG3*[C-terminal region of CH2: >aa position 251]-human-IgG3*[CH3],
rat-IgG2b/mouse-[VH-CH1,VL-CL]-human-IgG1-[hinge-CH2-CH3],
rat-IgG2b/mouse-[VH-CH1,VL-CL]-human-IgG2-[hinge-CH2-CH3],
rat-IgG2b/mouse-[VH-CH1,VL-CL]-human-IgG3-[hinge-CH2-CH3, oriental allotype],
rat-IgG2b/mouse-[VH-CH1,VL-CL]-human-IgG4-[hinge-CH2-CH3],
human-IgG1/human-[VH-CH1,VL-CL]-human-IgG1-[hinge]-human-IgG3*-[CH2-CH3],
human-IgG1/rat-[VH-CH1,VL-CL]-human-IgG1-[hinge]-human-IgG4 [N-terminal region of CH2]-human-IgG3*[C-terminal region of CH2: >aa position 251]-human-IgG3*[CH3]
human-IgG1/mouse-[VH-CH1,VL-CL]-human-IgG1-[hinge]-human-IgG4[N-terminal region of CH2]-human-IgG3*[C-terminal region of CH2: >aa position 251]-human-IgG3*[CH3],
human-IgG1/rat-[VH-CH1,VL-CL]-human-IgG1-[hinge]-human-IgG2[N-terminal region of CH2]-human-IgG3*[C-terminal region of CH2: >aa position 251]-human-IgG3*[CH3],
human-IgG1/mouse-[VH-CH1,VL-CL]-human-IgG1-[hinge]-human-IgG2[N-terminal region of CH2]-human-IgG3*[C-terminal region of CH2: >aa position 251]-human-IgG3*[CH3],
human-IgG1/rat-[VH-CH1,VL-CL]-human-IgG1-[hinge]-human-IgG3*-[CH2-CH3],
human-IgG1/mouse-[VH-CH1,VL-CL]-human-IgG1-[hinge]-human-IgG3*-[CH2-CH3],
human-IgG2/human-[VH-CH1,VL-CL]-human-IgG2-[hinge]-human-IgG3*-[CH2-CH3], human-IgG4/human-[VH-CH1,VL-CL]-human-IgG4-[hinge]-human-IgG3*-[CH2-CH3],
human-IgG4/human-[VH-CH1,VL-CL]-human-IgG4-[hinge]-human-IgG4[N-terminal region of CH2]-human-IgG3*[C-terminal region of CH2: >aa position 251]-human-IgG3*[CH3],
mouse-IgG2b/rat-[VH-CH1,VL-CL]-human-IgG1-[hinge]-human-IgG3*-[CH2-CH3],
mouse-IgG2b/human-[VH-CH1,VL-CL]-human-IgG1-[hinge]-human-IgG3*-[CH2-CH3],
mouse-IgG2b/mouse-[VH-CH1,VL-CL]-human-IgG1-[hinge]-human-IgG3*-[CH2-CH3],
mouse-[VH-CH1,VL-CL]-human-IgG4/rat-[VH-CH1,VL-CL]-human-IgG4-[hinge]-human-IgG4-[CH2]-human-IgG3*-[CH3],
human-IgG1/rat-[VH-CH1,VL-CL]-human-IgG1-[hinge]-human-IgG4-[CH2]-human-IgG3*-[CH3],
human-IgG1/mouse-[VH-CH1,VL-CL]-human-IgG1-[hinge]-human-IgG4-[CH2]-human-IgG3*-[CH3],
human-IgG4/human-[VH-CH1,VL-CL]-human-IgG4-[hinge]-human-IgG4-[CH2]-human-IgG3*-[CH3],
rat-IgG2b/mouse-IgG2a,
rat-IgG2b/mouse-IgG2b, and
rat-IgG2b/mouse-IgG3.

22. The method of claim 21, wherein the peripheral blood mononucleated cells are added following a preincubation of the thus-treated tumor cells with said intact heterologous bispecific antibodies.

* * * * *